United States Patent [19]
Rowland

[11] Patent Number: 5,027,800
[45] Date of Patent: Jul. 2, 1991

[54] MAN'S ERECTION TRUSS

[76] Inventor: Harold L. Rowland, 4928 S. 293rd, Auburn, Wash. 98001

[21] Appl. No.: 411,417

[22] Filed: Sep. 22, 1989

[51] Int. Cl.⁵ .................................................. A61F 5/41
[52] U.S. Cl. ...................................................... 128/79
[58] Field of Search ........................................... 128/79

[56] References Cited

U.S. PATENT DOCUMENTS

| | | | |
|---|---|---|---|
| 1,410,339 | 3/1922 | Martinka | 128/79 |
| 2,581,114 | 1/1952 | Larson | 128/79 |
| 3,461,863 | 8/1969 | Sullinger | 128/79 |
| 3,636,948 | 1/1972 | Atchley | 128/79 |
| 3,773,040 | 11/1973 | Gavrilovich | 128/79 |
| 3,939,827 | 2/1976 | Brunstetter | 128/79 |
| 4,139,007 | 2/1979 | Diamond | 128/79 |
| 4,362,152 | 12/1982 | Gorokhovsky et al. | 128/79 |
| 4,872,447 | 10/1989 | Tsirjulnikov et al. | 128/79 |

FOREIGN PATENT DOCUMENTS

| | | | |
|---|---|---|---|
| 158658 | 9/1954 | Australia | 128/79 |
| 440947 | 5/1925 | Fed. Rep. of Germany | 128/79 |

Primary Examiner—Cary E. Stone

[57] ABSTRACT

A man's erection truss to be temporarily worn by a man, helping him to acquire and to maintain his turgidity during copulation is provided by a manufacturer in a kit requiring final fitting and completion by the man, with or without the assistance of a physician or another person. When completed, this erection truss is essentially a completed loop of surgical tubing, or the like, having a male-female, preferably plastic, in line encirclement fastener assembly, removably fastened, thereby permitting repeated uses, while maintaining essentially the same fit. The kit includes a rigid plastic fitting assembly of two parallel tubes attached to one another, having one end of each rigid tube located adjacent one another, and the other ends being longitudinally spaced, as one rigid tube is preferably longer than the other. The surgical tubing is knotted at one end, passed through the shorter rigid tube, then formed into a large loop, and thereafter passed through the longer rigid tube. The formed larger loop is moved over the penis and behind the testicles while being positioned by the fitting assembly. Then the unknotted, other end, i.e. free end, of the surgical tubing is pulled, until the loop fits tightly. Thereafter, the surgical tubing is marked nearby the adjacent ends of the rigid side by side plastic tubes, and then the surgical tubing is pulled in the reverse direction. The resulting enlarged loop is removed, and the surgical tubing is removed from the two parallel rigid tubes. The removed surgical tubing is then cut at one mark, and cut a quarter of an inch beyond the other mark. Thereafter, this custom length of surgical tubing has the female and male portions of the insertable pull apart in line encirclement fastener assembly respectively glued to its respective ends, to become the custom fitted man's erection truss, which, when in use, does not interfere with the mutual enjoyment experienced by the man and his spouse.

15 Claims, 2 Drawing Sheets

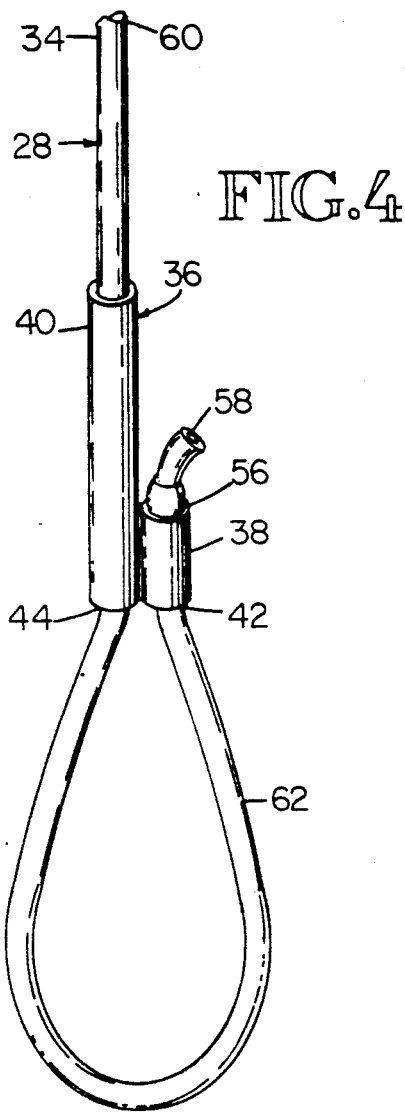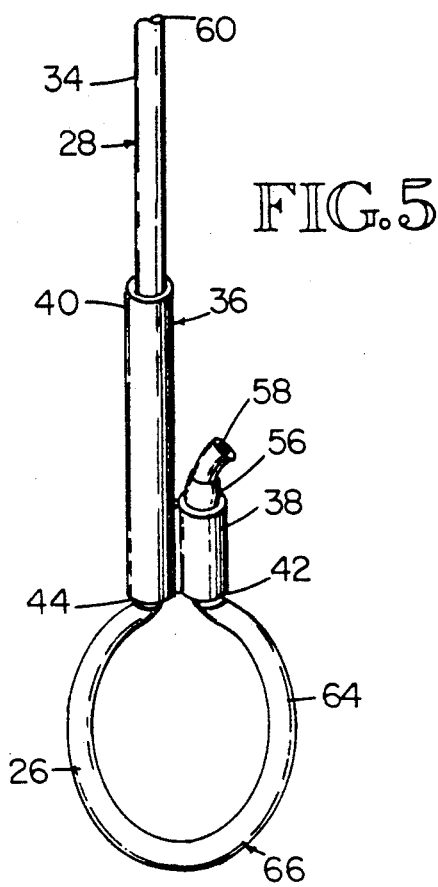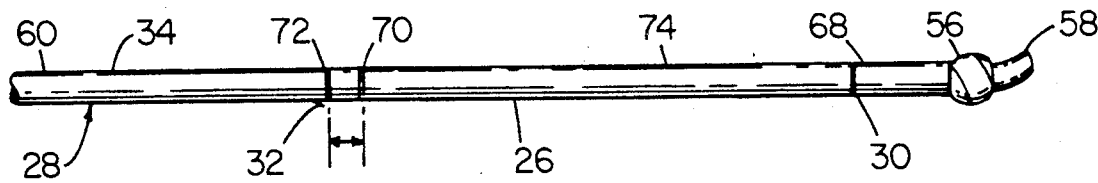

MAN'S ERECTION TRUSS

BACKGROUND

In the past and also presently used are several types of products temporarily worn by a man to maintain his turgidity during his times of wanted male potency. Some are used under the guidance of a physician and are considered therapeutic products, and some of these require surgical procedures. Others may or may not be used under the guidance of a physician. Some examples of such products, as set forth in U.S. patents are:

In 1926, Peter W. Nelson in his patent 1,608,806, illustrated and described his surgical appliance consisting of an elastic apron having an extending central elastic sleeve. The sleeve surrounded the penis and the apron surrounded the neck of the scrotum. Upon wearing this surgical appliance the inflowing blood of a male passing through the deep laying arteries was dammed, and the back flow was retarded or checked, through the veins lying close to the upper surface of the penis.

In 1951, William P. Laser in his patent 2,576,024, disclosed his scrotum sleeve. A "C"-shaped member received the scrotum and a plug was later used to change the "C"-shape to an annulus shape.

In 1952, Leroy J. Larson illustrated and described his surgical device as set forth in his patent 2,581,114. When it was applied to a penis, the free flow of blood to the erectile tissues of the penis continued; however, the return of the blood to the main body portion was interrupted upon the restriction of the dorsal veins of the penis. This surgical device had a specially formed flexible tube surrounding, in part, two inserted balls, selectively positioned apart, during sizing this surgical device to a person. One of the balls created localized pressure against the penis and the other ball served as a portion of a fastening combination.

In 1969, Glen R. Sullinger in his patent 3,461,863, discussed and illustrated his turgidity-maintaining tourniquet. He used surgical rubber with a curved portion of a rigid plastic, to create the tourniquet to be tightened about the penis near the scrotum.

In 1972, Otto Atchley in his patent 3,636,948, presented his therapeutic device, which was a specially formed adjustable diameter resilient band. It was tightly wrapped around the penis near the pubic bone. It had projections on the inner surface positioned to restrict the flow of blood from the penis, thereby helping in achieving the erection of the penis.

In 1974, Richard K. McIntire in his patent 3,799,157, illustrated and described his therapeutic genital device worn to maintain the human penis in an erect condition by damming the blood from flowing back into the trunk of one's body. Two interconnected bands of leather, or leather-like materials, were equipped with fasteners to snugly position one loop of one band about the base of the penis, and to snugly position the other loop of the other band about the neck of the scrotum.

Also in 1974, Joao Birman in his patent 3,845,760, disclosed his loop for erecting a male member to reduce the incidence of impotency. The overall loop compressed a band to essentially surround the penis, an elastic ring carried by a cord and positioned adjacent one end of the band, and a cord secured to the band at this ring, and thereafter threaded through a hole at the other end of the band, and returned to and through the elastic ring and secured.

In 1978, Robert J. Woodward in his patent 4,102,335, presented his male potency device formed of an adjustable size bimetallic ring.

In 1979, Harvey Diamond, in his patent 4,139,007, illustrated and disclosed his method and apparatus for contraception. He created an adjustable pressure pad made of an elastomer, so molded to provide a strap portion and a pressure pad portion. The latter brought pressure to the urethra without unduly pressing on the corpus cavernosa.

In 1982, Veniamin Gorokhovsky and Gregory Fradkin, in their patent 4,362,152, disclosed their erector, which was a prosthetic erector for remedying problems of impotency in men. They used a pair of rigid rods encased within a common elastic encasement in a side by side relationship.

These illustrations and descriptions of these patents are considered representative of what products, persons at earlier times, provided to men to try to remedy their impotency. There remains a need, however, for such a like purpose product, to be partially created by a manufacturer and then sold to a customer, who himself or with the services of a physician or other persons, creates his own custom product to assist him in overcoming his impotency, without interfering with the mutual enjoyment experienced by himself and his spouse.

SUMMARY

A kit is provided by a manufacturer to be sold to or for a man to assist him in preparing an erection truss to help him in overcoming his impotency. He alone, or with the assistance of another person, such as a physician, will use the components of the kit, which may or may not include a measuring device, a position marker, a pair of scissors, and a tube of glue, but which will always include, a length of surgical tubing or like tubing, a set of attached parallel side by side rigid plastic tubes, one longer than the other, and a set of male and female fasteners, each insertable in part into the other, and each in part to be covered with glue and inserted in part into respective ends of a correctly sized length of the surgical tubing, to create this man's erection truss.

The surgical tubing is knotted at one end. The other end is threaded through the shorter one of the parallel side by side rigid plastic tubes, emerging at a tube end, which is adjacent the tube end of the longer one of these parallel side by side rigid plastic tubes. Then this other end, moving as a free end, is formed into a large loop and thereafter threaded through the longer tube commencing at the end, which is adjacent to the end of the shorter one of these parallel side by side rigid plastic tubes.

This assembly of the surgical tubing and the side by side rigid plastic tubes is moved, so the large loop is moved over the man's penis and behind his testicles. Thereafter, the other end, the free end, is pulled to decrease the side of the loop, until the surgical tubing fits tightly, but not too tight. Using a marker, such as a felt pen, the tubing is marked at both locations of the adjacent ends of the shorter and longer parallel side by side rigid plastic tubes.

Then this assembly, as so marked, is released from the man upon reversing the direction of motion of the surgical tubing passed through the longer one of the rigid plastic tubes. Thereafter, the marked surgical tubing is cleared from the parallel side by side rigid plastic tubes. Then the plastic tubing is cut at one mark. Then the plastic tubing is marked again, one quarter of an inch farther from the remaining mark of the original two. Thereafter, at this new mark, i.e. the third mark, the surgical tubing is cut, to complete a length of surgical tubing, which, if then formed into a circle, reaches the desired circumferential length of a comfortable fitting man's erection truss.

To so hold the cut ends of this proper length of surgical tubing together, after fitting a man, a fastener assembly has been made of preferably two plastic portions, one male and one female. Each overall portion has its telescoping gripping portion for interfitting with the other overall portion, and its gluable portion for interfitting with an end of the surgical tubing. The gluable portions are covered sufficiently with glue and inserted into the respective ends of the surgical tubing. When the glue is dry, the erection truss is then ready to be positioned for the first time, and many times thereafter, about the man's penis and behind his testicles.

The fastener assembly, to be fastened, requires in line opposite pushing forces, and to be unfastened requires in line opposite pulling forces. During use of this man's erection truss during copulation, any possible occurring in line opposite pulling forces are not strong enough to cause an unwanted unfastening of this man's erection truss.

During each successive use of this man's erection truss, for several times, this erection truss remains essentially always the right comfortable loop size. The overall preferable all plastic manufacture creates a very comfortable erection truss, which is to be worn only during the intended copulation periods. The erection truss is readily, easily, and successfully cleaned after each use. Preferably, this man's erection truss is stored in a writing pen like appearing container, while awaiting another successful use period.

DRAWINGS

This man's erection truss, in a preferred embodiment is illustrated in the drawings, inclusive of its presentation as a kit, wherein.

Figure 1:
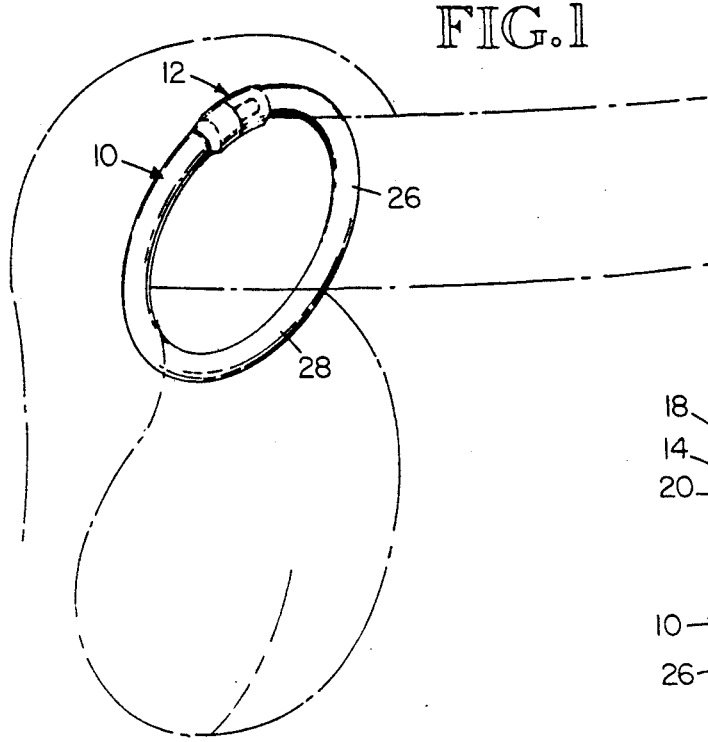
FIG. 1 is a perspective view of the man's erection truss in its fitted position, with phantom lines indicating portions of a man's body which are adjacent to this installed erection truss, i.e. the lower body, the penis, the scrotum, and testicles.
Figure 2:
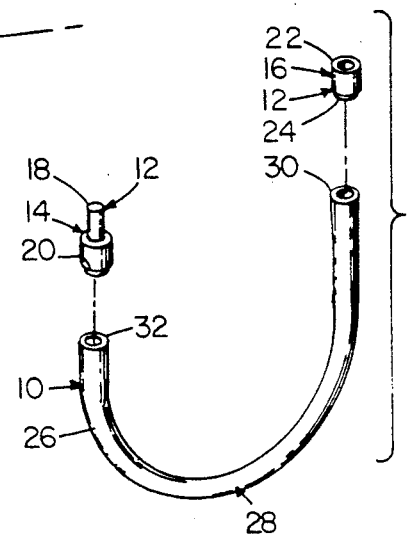
FIG. 2 is a perspective exploded view of the man's erection truss in a loop like arrangement with the separated male and female portions of an in line encirclement fastener assembly.
Figure 3:
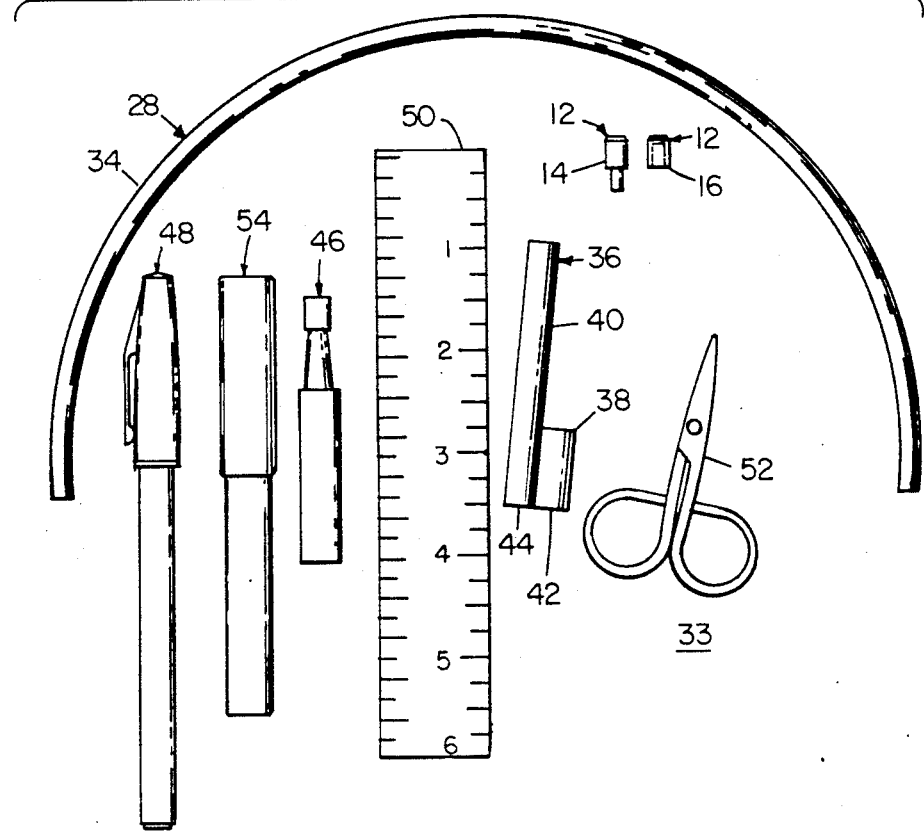

FIG. 3 is a planar view on a reduced scale, of a portion of a table top on which the components of a selected kit have been removed from a box, not shown, and spaced apart, i.e. a starting length of surgical tubing, the male and female portions of the in line encirclement fastener assembly, the rigid plastic fitting assembly of the longitudinally side by side parallel tubes, each having an end adjacent the end of the other, and one rigid tube being shorter than the other rigid tube, a tube of glue, a marking pen, a ruler, scissors, and a writing pen like container to receive the completed man's erection truss;

FIG. 4 is a perspective of the starting length of surgical tubing arranged in the rigid plastic fitting assembly showing a knotted end thereof threaded through the shorter tube, the formation of a large loop of the surgical tubing passed over the penis and testicles, the other free end of the surgical tubing being passed through the longer tube and beyond;

FIG. 5 is a perspective view like the view in FIG. 4, but showing the fitted tightened loop of surgical tubing being marked twice, respectively, adjacent the respective adjacent ends of the shorter and longer parallel rigid tubes; and FIG. 6 is a planar view of the removed starting length of the surgical tubing having been marked again, with the third mark being one quarter of an inch beyond the second mark, and thereafter, as not shown, this starting length of the surgical tubing is cut at the first and third marks, with the second mark being cleaned away, to create the custom length of the surgical tubing shown in FIGS. 1 and 2, which is then ready to be glued to the in line encirclement fastener assembly.

DESCRIPTION OF THE PREFERRED EMBODIMENT

In FIGS. 1 through 6, a preferred embodiment of the man's erection truss 10 is illustrated. It is shown in its fitted position in FIG. 1 placed over the penis and behind the testicles. This truss 10 is easily fastened and unfastened by utilizing the in line encirclement fastener assembly 12, shown in FIGS. 1, 2, and 3. There are male and female portions 14, 16, of this assembly 12. The male portion 14 has a male interfitting portion 18 and a glue receiving portion 20. The female portion 16 has a female interfitting portion 22 and a glue receiving portion 24.

The encircling body 26 of the truss 10 is made of surgical tubing 28, or like tubing. The in line encirclement fastener assembly 12 is preferably made of rigid plastic, and the male and female portions 14, 16, are preferably glued to ends 30, 32 of the surgical tubing 28 cut to form the custom length of the encircling body 26 of this man's erection truss 10, as shown in FIGS. 1 and 2.

Because each man needs a custom fit, the manufacturer supplies a man or his physician, with some or all of the components, originally packaged in a box, not shown, as they are shown spaced apart on a table top 33 in FIG. 3. There are an original long starting length 34 of surgical tubing; the male and female portions 14, 16 of the in line encirclement fastener assembly 12; the rigid plastic fitting assembly 36 of the longitudinally side by side parallel tubes 38, 40, each having an end adjacent the end of the other, 42, 44, and one rigid tube 38 being shorter than the other, i.e. longer, rigid tube 40; and then the selective optionally provided tube of glue 46; marking pen 48; ruler 50, scissors 52; and a writing pen like container 54 to receive and to carry the completed man's erection truss 10.

In making the custom length of the encircling body 26 of surgical tubing 28, the original long starting length 34 of the surgical tubing 28, first has a knot 56 tied in one end 58. Then the other end, i.e. the free end 60, of the starting length 34, is threaded through the shorter tube 38, until the knot 56 stops this threading. Thereafter, this starting length 34 creates a large loop 62 as the free end 60 is threaded through the longer tube 40, as shown in FIG. 4.

This large loop 62 is passed over the penis and testicles while the surgical tubing 28 is being positioned by the rigid plastic fitting assembly 36. Then, when this position is reached, the free end 60 is pulled to tightly fit portions of the surgical tubing 28 in place about the respective body portions, as illustrated in FIG. 4, creating the small loop 64.

A marking pen 48 is then used to mark the surgical tubing twice adjacent the respective ends 42, 44 of the shorter rigid tube 38 and of the longer rigid tube 40. Thereafter, the tightly fitting portions of the surgical tubing 28, forming the small loop 64, are pulled clear by recreating the large loop 62.

This marked overall assembly 66 of the marked surgical tubing 28 and the rigid plastic fitting assembly 36, having been removed from the man, is then disassembled by unthreading the original long length of surgical tubing 34 from the rigid plastic fitting assembly 36. Thereafter, this removed starting length of surgical tubing 34 is laid in a linear configuration, as shown in FIG. 6. It is then marked a third time, using the ruler 50, by making a third mark 72 with the marking pen 48, one quarter of an inch beyond the second mark 70, thereby presenting the three marks 68, 70, and 72.

The selected proper length 74 of the surgical tubing 34 to create the encircling body 26 of the man's erection truss 10 is then made by using the scissors 52 to cut the surgical tubing 28 at the marked locations 68 and 72. Thereafter, the second mark 70 is cleaned away, completing the length of the encircling body 26.

Then the glue receiving portion 20 of the male portion 14, and the glue receiving portion 24 of the female portion 16, of the in line encirclement fastener assembly 12, are coated with glue, by using some of the contents of the tube of glue 46. Thereafter, these glue covered portions 20 and 24 are inserted into the ends 30, 32 of this cut to size surgical tubing 74, used in forming the encircling body 26. After a drying period, the custom fitted man's erection truss 10 is ready for the first of many times of use. After its encircling position is about to be reached, the male interfitting portion 18 and the female interfitting portion 22 are in line circumferentially moved together to complete the interfitting of the male portion 14 and female portion 16, and thereby to complete the fitting of the man's erection truss 10. It is left in such fitting place only during the overall copulation period, and during copulation this man's erection truss 10 does not cause any discomfort to interfere with the mutual enjoyment experienced by the man and the woman. After cleaning, the man's erection truss 10 is optionally placed in the writing pen like container 54.

I claim:

1. A man's erection truss to be temporarily worn by a man, helping him to acquire and to maintain his turgidity, comprising:
    (a) surgical tubing, or like tubing, custom fitted to be a tight fit, when fitted over the penis and behind the testicles, having one radial plane cut creating adjacent ends thereof, and
    (b) an in line encirclement fastener assembly having male and female portions thereof, respectively entirely glued on their exteriors to the respective interiors of the adjacent ends of the surgical tubing, so these ends will continue to abut one another, to complete this reusable custom fitted man's erection truss.

2. A man's erection truss, as claimed in claim 1, wherein the in line encirclement fastener assembly is made so these male and female portions will conform to the shape of the surgical tubing so the custom fit thereof remains.

3. A man's erection truss, as claimed in claim 2, wherein the in line encirclement fastener assembly has the male and female portions formed with interfittings surfaces thereof, having roughened surfaces for enhancing and creating their holding power when telescoped together, throughout many cycles for fastening and unfastening of this truss.

4. A kit having materials, a fitting assembly, and a fastener assembly all used to create a custom fitted man's erection truss, comprising:
    (a) a length of surgical tubing, or like tubing;
    (b) a fitting assembly having two parallel tubes attached lengthwise to one another, with one tube being longer than the other, and both having one end opposite the end of the adjacent tube; and
    (c) a fastener assembly having insertable and pull apart female and male portions thereof, and having respective portions on each female and male portion adapted to receive glue and be inserted within cut ends of a custom cut length of the surgical tubing.

5. A kit, as claimed in claim 4, wherein the fastener assembly is an in line encirclement fastener assembly.

6. A kit, as claimed in claim 5, wherein the two parallel tubes are made of rigid plastic materials.

7. A kit, as claimed in claim 6, wherein the in line encirclement fastener assembly is made of plastic materials.

8. A kit, as claimed in claim 7, wherein the in line encirclement fastener assembly has the plastic male and female portions formed with interfitting surfaces thereof, having roughened surfaces for creating their holding power when telescoped together.

9. A kit, as claimed in claim 8, having a tube of glue to be used in securing the in line encirclement fastener assembly to cut ends of a custom cut length of the surgical tubing.

10. A kit, as claimed in claim 9, having a marking means to be used in marking the original length of surgical tubing to determine what custom cut length of this tubing is to be obtained in creating a custom fitted man's erection truss.

11. A kit, as claimed in claim 10, having a cutting means to be used in cutting the original length of surgical tubing, in reference to the markings, to create the custom cut length of this tubing in providing this custom fitted man's erection truss.

12. A kit, as claimed in claim 11, having a measuring means, to be used in determining the length of the custom cut length of the surgical tubing.

13. A method of making a man's erection truss to be temporarily worn by a male, helping him to acquire and to maintain his turgidity, comprising:
    (a) selecting a length of surgical tubing, or like tubing, having one end to be knotted and the other end to be free;
    (b) providing side by side longitudinally arranged rigid tubes each having one end thereof adjacent one another;
    (c) tying a knot in one end of the surgical tubing;
    (d) threading the other free end through one of the side by side rigid tubes;
    (e) moving this free end to form an enlarged loop;
    (f) threading this other free end through the other one of the side by side rigid tubes, whereby a circumferential length of surgical tubing is determined extending between the rigid tube ends that are adjacent one another;
    (g) placing the enlarged loop of surgical tubing over the penis and behind the testicles;
    (h) pulling the surgical tubing to create a tight fit;
    (i) providing a marking means;

(j) using the marking means to mark the surgical tubing adjacent the rigid tube ends, creating the first two marks;

(k) pulling, in the reverse direction, the surgical tubing to enlarge the loop thereof;

(l) clearing the enlarged loop of surgical tubing from behind the testicles and over the penis;

(m) unthreading the surgical tubing from the side by side longitudinally arranged rigid tubes;

(n) providing a measuring means;

(o) marking the surgical tubing a third time to extend the distance one quarter of an inch beyond the length between the first two marks;

(p) providing a cutting means;

(q) cutting the surgical tubing at the first and third marks to create the custom length of surgical tubing for creating an encirclement having one joint at a radial plane, determined by the cut ends of this surgical tubing;

(r) providing an in line encirclement fastener assembly having male and female portions thereof;

(s) gluing the respective male and female portions of the in line encirclement fastener assembly to the respective cut ends of this surgical tubing, to thereby complete this man's erection truss.

14. A method of making a man's erection truss, as claimed in claim 13, wherein, in providing the in line encirclement fastener assembly, plastic materials are provided in making the male and female portions thereof.

15. A method of making a man's erection truss, as claimed in claim 14, wherein, in providing the plastic male and female portions of the in line encirclement fastener, interfitting portions thereof are roughened, to provide surfaces which increase their holding power when fastened together.

* * * * *